United States Patent [19]
Rajaiah et al.

[11] Patent Number: 5,880,172
[45] Date of Patent: Mar. 9, 1999

[54] DENTURE STABILIZING COMPOSITIONS

[75] Inventors: Jayanth Rajaiah, Loveland; David Alan Nichols; Kimberly Ann Gilday-Weber, both of Cincinnati, all of Ohio

[73] Assignee: The Procter & Gamble Company, Cincinnati, Ohio

[21] Appl. No.: 738,153

[22] Filed: Oct. 25, 1996

Related U.S. Application Data

[63] Continuation-in-part of Ser. No. 330,470, Oct. 28, 1994, abandoned.

[51] Int. Cl.⁶ .............................. A61K 6/00; B32B 27/36
[52] U.S. Cl. ............................................ 523/120; 428/483
[58] Field of Search .............................. 428/483; 523/120

[56] References Cited

U.S. PATENT DOCUMENTS

| | | |
|---|---|---|
| 1,917,902 | 7/1933 | Rowe et al. . |
| 2,866,775 | 12/1958 | Sellers . |
| 2,897,593 | 8/1959 | Hollander et al. ............................. 32/2 |
| 3,575,915 | 4/1971 | Novak et al. ........................... 260/29.6 |
| 3,736,274 | 5/1973 | Schoenholz et al. .................. 260/17 R |
| 3,990,149 | 11/1976 | Nedwig .......................................... 32/2 |
| 4,136,163 | 1/1979 | Watson et al. ............................. 424/54 |
| 4,202,098 | 5/1980 | Russo ....................................... 433/168 |
| 4,373,036 | 2/1983 | Chang et al. ............................ 523/120 |
| 4,503,116 | 3/1985 | Lapidus .................................... 428/286 |
| 4,529,748 | 7/1985 | Wienecke ................................. 523/120 |
| 4,632,880 | 12/1986 | Lapidus .................................... 428/286 |
| 4,758,630 | 7/1988 | Shah et al. ............................... 525/207 |
| 4,772,470 | 9/1988 | Inoue et al. .............................. 424/435 |
| 4,880,702 | 11/1989 | Homan et al. ........................... 428/354 |
| 5,073,604 | 12/1991 | Holeva et al. ......................... 525/327.8 |
| 5,093,387 | 3/1992 | Schobel et al. .......................... 523/120 |
| 5,158,825 | 10/1992 | Altwirth .................................. 428/286 |
| 5,166,233 | 11/1992 | Kuroya et al. ............................. 524/37 |
| 5,204,414 | 4/1993 | Pelah et al. ........................... 525/327.8 |
| 5,209,777 | 5/1993 | Altwirth .................................... 106/35 |
| 5,298,534 | 3/1994 | Prosise et al. ........................... 523/120 |
| 5,369,145 | 11/1994 | Gasman et al. ......................... 523/120 |
| 5,525,652 | 6/1996 | Clarke et al. .............................. 524/37 |

FOREIGN PATENT DOCUMENTS

| | | | |
|---|---|---|---|
| 0353375 | 2/1990 | European Pat. Off. ........ A61C 13/23 |
| 0 555 019 A1 | 8/1993 | European Pat. Off. ......... A61K 6/00 |
| 3613432 SHO | 10/1987 | Germany ....................... A61C 13/23 |
| 63-54318 | 3/1988 | Japan ............................... A61K 9/70 |
| Hei 4-149110 | 5/1992 | Japan . |
| Hei 5-65210 | 3/1993 | Japan . |
| Hei 5-65211 | 3/1993 | Japan . |
| WO 96/04883 | 2/1996 | WIPO ............................ A61K 6/087 |

OTHER PUBLICATIONS

08/330,492 (Case 5465), Rajaiah, et al., Oct. 28, 1994.
08/677,713 (Case 6172), Rajaiah, et al., Jul. 8, 1996.
08/824,940 (Case 6565), Liang, et al., Mar. 27, 1997.
08/835,041 (Case 6564), Liang, et al., Mar. 27, 1997.

*Primary Examiner*—Veronica P. Hoke
*Attorney, Agent, or Firm*—Betty J. Zea; Mary Catherine Hentz; Douglas C. Mohl

[57] ABSTRACT

The present invention relates to a denture adhesive composition comprising a lower alkyl vinyl ether-maleic acid, anhydride, or salt polymer or mixtures thereof, and at least one non-adhesive self-supporting layer. The present invention also relates to a denture adhesive composition comprising at least one non-adhesive self-supporting layer and at least two adhesive components wherein one of the adhesive components is a lower alkyl vinyl ether-maleic acid, anhydride or salt polymer of mixtures thereof.

42 Claims, No Drawings

DENTURE STABILIZING COMPOSITIONS

This is a Continuation-in-Part of application Ser. No. 08/330,470, filed Oct. 28, 1994 now anandoned.

BACKGROUND OF THE INVENTION

Ordinary removable dentures, dental plates and the like, comprise teeth mounted in a suitable plate or base. Although dentures generally are skillfully prepared, often they do not fit perfectly. Moreover, no matter how satisfactory at first, after a period of time the fit of the denture becomes loose and imperfect due to natural shrinkage and changes in the gums, underlying bone structure, mucous tissues, and the like. Loose and imperfectly fitted dentures can be corrected and stabilized by the use of a denture stabilizer. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Several deficiencies commonly exist with denture stabilizing or adhesive compositions. Common aesthetic deficiencies include oozing of the adhesive from under the dental plate during insertion and throughout the wearing period and messiness and difficulty of removing the residual adhesive from the mouth and dentures. Additionally, food may become trapped between the denture and the oral cavity of the wearer.

Considerable effort has been made over the years to develop improved denture adhesive compositions. Both synthetic and natural polymers and gums have been used singly, in combination, and in combination with various adhesives and other materials in an attempt to lessen the deficiencies noted above.

U.S. Pat. No. 4,880,702 to Homan et al., issued Nov. 14, 1989 discloses a denture stabilizer in the form of a strip consisting of three layers. The two outside layers consist of a polymer selected from the group consisting of polyethylene oxide having an average molecular weight of about 200,000 to 10,000,000, sodium carboxymethylcellulose, polyvinyl alcohol, and mixtures thereof. The inside layer consists of microcrystalline wax and a polymer sufficient to adhere the inside layer to gums and a denture base, after contact with water, when the outside layers have been dissolved. European Patent Application 0,353,375 to Altwirth published Feb. 7, 1990, discloses an adhesive insert for dentures consisting of a adhesive permeated fibrous fleece and an adhesive consisting of a pasty mixture of alginate and/or carboxymethylcellulose, polyvinyl acetate and an alcoholic solvent. Despite the above-noted technologies as well as many others, need still exists for improved denture stabilizing compositions which offer a secure hold and are aesthetically pleasing to the user and which ooze less than currently available products.

It has been discovered, in accordance with the present invention, that a denture adhesive composition can be formulated having excellent adhesive quality. These adhesive compositions effectively stabilize dentures while oozing less and providing pleasing aesthetics to the user. The invention denture adhesive compositions may also be effectively used as a wound dressing, underwater adhesive, a bioadhesive, and/or as a delivery vehicle for other actives.

It is an object of the present invention to provide a denture adhesive composition which effectively holds dentures in place for a prolonged period of time yet allows for easy removal of the denture on demand. It is also an object of the invention to provide an improved adhesive composition which may be used with dentures and which oozes less during insertion and wear than currently available stabilizers and is aesthetically pleasing to the user.

These and other objects of the present invention will become readily apparent from the detailed description which follows.

SUMMARY OF THE INVENTION

The present invention relates to a denture adhesive composition comprising a lower alkyl vinyl ether-maleic acid, anhydride, or salt polymer or mixtures thereof, and at least one non-adhesive self-supporting layer. The present invention also relates to a denture adhesive composition comprising at least one non-adhesive self-supporting layer and at least two adhesive components wherein one of the adhesive components is a lower alkyl vinyl ether-maleic acid, anhydride or salt polymer of mixtures thereof.

DETAILED DESCRIPTION OF THE INVENTION

The denture adhesive compositions of the present invention comprise a lower alkyl vinyl ether-maleic polymer and at least one non-adhesive self-supporting layer. Preferably the lower alkyl vinyl ether-maleic polymer is in salt form. It is also preferred that the present compositions comprise at least two adhesive components wherein one of the adhesive components is a lower alkyl vinyl ether-maleic acid, anhydride or salt polymer (or mixtures thereof).

The present denture adhesive compositions are thoroughly moistened and applied to dentures. The attachment of the adhesive component to the non-adhesive self-supporting layer provides a composition which may ooze less in the oral cavity than conventional adhesive creams which contain oily carrier vehicles. This attachment also provides a composition which is easy to clean from dentures since the non-adhesive self-supporting layer maintains its strength and integrity in the presence of water and/or saliva, and allows the composition to be peeled from the dentures upon their removal. A detailed description of essential and optional components of the present invention is given below.

Non-Adhesive Self-Supporting Layer

The present denture adhesive compositions comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include such materials as polyester, polypropylene, nylon, rayon, cellulose acetate, cellulose derivatives, cloth, fibrous fleece, paper, plastic, leather, microcrystalline wax, synthetic fibers, natural fibers, and mixtures thereof. Preferred are cellulose derivatives, polyester, polypropylene, nylon, rayon, cloth, paper, microcrystalline wax, and mixtures thereof. Most preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

Adhesive Component

The present denture adhesive compositions comprise a lower alkyl vinyl-ether maleic acid, anhydride, or salt polymer or mixtures thereof. In a preferred embodiment the present compositions may comprise at least two adhesive components where one of the adhesive components is a lower vinyl ether-maleic acid, anhydride or salt polymer, or mixtures thereof. A detailed description of these components is provided below.

Lower Alkyl Vinyl Ether-Maleic Polymer

The lower alkyl vinyl ether-maleic ("AVE/M") polymers useful in the present invention may be in either acid, anhydride and/or salt form. The salt form is preferred for use in the present compositions. The salt form of the polymer comprises a cationic salt function. Suitable cations include calcium, sodium, magnesium, potassium, ammonium, zinc, strontium, iron, and mixtures thereof. Preferred are zinc, strontium, calcium, and sodium, and mixtures thereof. Salts of lower alkyl vinyl ether-maleic acid polymers are also described in U.S. Pat. No. 5,073,604 to Holeva et al., issued Dec. 17, 1991, which is incorporated herein by reference.

The polymer salts may be mixed or unmixed or both. The term "unmixed polymer salts" as used herein refers to salts of lower alkyl vinyl ether-maleic polymers wherein the cations are unmixed with any other ester functions or nonidentical cations on the same polymer, the remaining carboxyl groups being unreacted.

The term "mixed polymer salts" as used herein refers to salts of the lower alkyl vinyl ether-maleic polymers where different cations are mixed on the same polymer with each other or with other ester functions. Preferred are mixed polymer salts containing zinc and calcium cations.

The cationic salt function may contain from about 0.1% to about 65% zinc, preferably from about 5% to about 45%, and most preferably from about 10% to about 30%, of the initial carboxyl groups reacted. The cationic salt function preferably further consists of from about 0.1% to about 75% metal salts selected from the group consisting of calcium, sodium, magnesium, strontium, potassium, ammonium, and mixtures thereof. Most preferred of the additional metal salts are calcium or sodium metal salts or mixtures thereof. Calcium cations may be present at a level of from about 10% to about 75%, preferably from about 25% to about 60%, and most preferably from about 40% to about 60%, of the total initial carboxyl groups reacted. Sodium cations may be present at a level of from about 1% to about 20%, preferably from about 1% to about 15%, and most preferably from about 1% to about 10%, of the total initial carboxyl groups reacted.

The lower alkyl vinyl ether-maleic acid polymer consists essentially of the repeated structural unit:

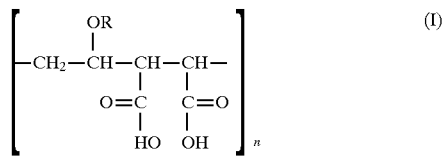

(I)

wherein R represents a C1 to C4 alkyl radical, n is an integer greater than one representing the number of repeated occurrences of the structural unit in a molecule of the polymer.

The lower alkyl vinyl ether maleic anhydride polymers are readily obtained by copolymerizing a lower alkyl vinyl ether monomer, such as methyl vinyl ether, ethyl vinyl ether, divinyl ether, propyl vinyl ether and isobutyl vinyl ether, with maleic anhydride to yield the corresponding lower alkyl vinyl ether-maleic anhydride copolymer which is readily hydrolyzable to the acid copolymer. Both anhydride and acid forms are also available from commercial suppliers. For example, the GAF Corporation, Wayne, N.J. provides both the polymeric free acid form (I) and the corresponding anhydride form under its "GANTREZ" trademark as the "GANTREZ S Series" and "GANTREZ AN Series", respectively. In the former acid series, the GANTREZ S-97 (M. W. TM 50,000) is particularly suitable, and, in the latter anhydride series, the GANTREZ AN-149 (M. W.=50,000) the GANTREZ AN-169 (M. W.=67,000) and the GANTREZ AN-179 (M. W.=80,000) copolymers are particularly suitable. The acid and anhydride forms of AVE/M polymers, having an average molecular weight of from about 50,000 to about 80,000 (as measured by membrane osmometry in 2-butanone 1–10 grams/1000 ml solution), are characterized by having the specific viscosity parameter of more than 1.2. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

The salt form of the subject polymers may be prepared by the interaction of the AVE/M anhydride polymer with at least one cationic salt function, such as zinc, strontium, calcium, sodium, magnesium, potassium, iron, or ammonium compounds having a functional group typical of reactants of a carboxylic acid, such as, for example, the hydroxide, acetate, halide, lactate, etc. in an aqueous medium. In a preferred embodiment, the oxide of zinc and the hydroxide of calcium are utilized. Since zinc hydroxide is not commercially available, its use as a reactant is readily and more economically accomplished by employing an aqueous slurry of particular zinc oxide which, although practically insoluble in water, provides hydration to zinc hydroxide on the particulate surface. Strontium hydroxide, on the other hand, is available in either crystalline or powder form and is soluble in about 50 parts water. Aqueous solutions of strontium oxide, however, which forms the hydroxide when treated with water (caution: heat evolution), may also be used.

Ions that form toxic, irritating or contaminating by-products should be avoided, or special precautions and treatment provided to assure the removal and absence of such by-products from the polymeric salt end-product. The particular compound used should be substantially pure to assure obtaining a substantially pure, substantially off-white polymeric salt end-product.

In general, the lower alkyl vinyl ether-maleic acid copolymer, or its corresponding anhydride, is added to water preheated to about 70°–80° C. with vigorous stirring to form a homogeneous mixture. If the anhydride precursor is utilized, it is recommended that the aqueous mixture be further heated to about 90° C. with stirring to ensure complete hydrolysis of the anhydride to the acid form. Heating is then discontinued although mixing is continued until the batch turns clear with a simultaneous decrease in viscosity (about 65°–75° C.).

If the salt form of the polymer is desired, an aqueous solution of the cationic salt forming compound, for example, an aqueous dispersion of particulate zinc oxide is combined with calcium hydroxide in the form of a slurry, in an amount sufficient to provide the desire cationic content desired in the end-product, is separately prepared at ambient temperature and slowly added to the hot polymeric acid solution with continuous vigorous mixing so as to prevent localized precipitation of the cationic polymeric salt. After addition is complete, mixing is continued to ensure that all the salt forming compound is reacted with the copolymer.

Alternatively, an aqueous solution containing the cationic salt function is preheated to 70°–80° C. with vigorous stirring to form a homogeneous slurry. The lower alkyl vinyl ether-maleic acid copolymer or its corresponding anhydride is then added to the slurry while further heating to 90° C. and stirring to ensure complete hydrolysis.

The reaction batch is then dried such as by shallow drying trays in a convection oven maintained at about 70° C. with hot air circulation to evaporate the water content and recover the polymeric salt product in dry form. Alternatively, the reaction batch is then transferred to 5 drum dryers maintained at 80–100 PSIG with hot steam to evaporate the water content and recover the polymer in the flake form. The resulting flakes may be subjected to milling and screening to yield the desired physical properties to provide satisfactory denture stabilizing properties.

The subject AVE/M polymers have exceptional adhesive qualities when contacted with water or saliva such that they are extremely useful as denture adhesive materials in denture stabilizing compositions. The AVE/M polymers may be utilized in effective adhesive amounts, preferably at least 20 percent by weight, and most preferably at least 30 percent by weight, as the sole adhesive component or as a co-adhesive in joint usage with other adhesive components.

Other Adhesive Components

The present invention compositions may also include other adhesive components. These adhesive components, if present, are used in safe and adhesively effective amounts. The term "safe and adhesively effective amount" as used herein means an amount sufficient to provide adherence to the oral cavity. In the present denture adhesive compositions, polyvinyl acetate is not included as a suitable "other adhesive component".

Suitable adhesive components include a water-soluble hydrophilic colloid or polymer having the property of swelling upon exposure to moisture to form a mucilaginous mass. Such adhesive materials include natural gums, synthetic polymeric gums, adhesive materials commonly employed in denture stabilizing compositions and compatible with the subject AVE/M polymers, synthetic polymers, mucoadhesive polymers, hydrophilic polymers, saccharide derivatives, cellulose derivatives, and mixtures thereof. Examples of such materials include karaya gum, guar gum, gelatin, algin, sodium alginate, tragacanth, chitosan, acrylamide polymers, carbopol, polyvinyl alcohol, polyamines, polyquarternary compounds, polybutenes, silicones, polyvinylpyrrolidone, cationic polyacrylamide polymers.

Preferred are cellulose derivatives such as methylcellulose, sodium carboxymethylcellulose, hydroxyethylcellulose, hydroxypropylcellulose, hydroxypropylmethylcellulose, carboxymethylcellulose. Most preferred are carboxy-methylcellulose, karaya gum, sodium alginate, chitosan, polyvinyl alcohol, and mixtures thereof. In general, the other adhesive components may be present at a level of from about 0% to about 70%, preferably from about 10% to about 50%, and most preferably from about 20% to about 40%, by weight of the composition.

Other Ingredients

One or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, preferably from about 1% to about 30%, by weight of the compositions.

The denture adhesive compositions may also be used as a denture adhesive and/or bioadhesive and comprise one or more therapeutic actives suitable for mucosal or topical administration. The phrase "suitable for mucosal or topical administration", as used herein, describes agents which are pharmacologically active when absorbed through internal mucosal surfaces of the body such as the oral cavity, or applied to the surfaces of the skin. Therapeutic actives may be present at a level of from about 0% to about 70%, by weight of the composition.

Therapeutic actives that are useful in these compositions include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; antifungals; aromatics such as camphor, eucalyptus oil, and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

The present denture adhesive compositions may also comprise coating which is sticky to dry dentures and, if present, will be placed on one side of the denture adhesive composition. Compositions suitable for use as the adhesive layer include polybutenes, silicones, rubbers, petrolatum, natural polymers, synthetic polymers, and mixtures thereof. The adhesive layer may be present at a level of from about 0% to about 70%, and preferably from about 0.5% to about 20%, by weight of the composition.

Other suitable ingredients include colorants, preservatives such as methyl and propyl parabens; thickeners such as silicon dioxide, and polyethylene glycol; and vehicles such as liquid petrolatum, petrolatum, mineral oil and glycerin. Preferred are polyethylene glycol, silicon dioxide, and petrolatum. Colorants, preservatives, thickeners and vehicles may be present at levels of from about 0% to about 20%, by weight of the composition.

The compositions of the present invention may also include one or more components which provide flavor, fragrance, and/or sensate benefit. Suitable components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxyamide agents such as N-ethyl-p-menthane-3-carboxamide which is described in U.S. Pat. No. 4,136,163 to Watson et. al., which is incorporated by reference herein in its entirety. These agents may be present at a level of from about 0% to about 50%, by weight of the composition.

Process for Preparation of the Composition

A process for the preparation of the present denture adhesive compositions comprises coating a weighed amount of the adhesive components onto the non-adhesive adhesive self-supporting layer.

The term "mixture", as used herein, refers to a solution, slurry, or suspension.

The adhesive components may be coated on the non-adhesive self-supporting supporting layer using various methods. These include: (a) wetting the non-adhesive adhesive self-supporting layer with water, uniformly sifting the adhesive component powder(s) onto the wet layer and then rewetting the layer with water; (b) dissolving the adhesive component(s) in water and/or other solvent(s) and coating the resulting mixture onto the layer; (c) coating the layer with the mixture produced during Gantrez® processing; (d) incorporating the adhesive component(s) into the layer as the layer is being formed; and (e) dissolving the adhesive component(s) in water and/or other solvent(s), wetting/coating the resulting mixture onto the layer, and uniformly sifting one or more adhesives in powder form onto the wet/coated layer and optionally re-coating/re-wetting the layer with the mixture and/or water; (f) the method of step (e) repeated multiple times; and (g) any combination of the methods in (a) through (f) above.

As disclosed above, the adhesive components may be dissolved in water and/or other solvents and the resulting mixture coated onto the layer. Solvents for the AVE/MA polymers include water and/or alcohols such as methanol, propanol, isopropanol, ethanol, butanol, 1,4-butanediol, cyclohexanol, and diethylene glycol; ethers or ether alcohols such as tetrahydrofuran, ethylene glycol monomethyl ether, diethylene glycol monomethyl ether, dioxane, and ethyl ether; esters such as methyl acetate, ethyl acetate and sec-butyl acetate; aldehydes, ketones or ketone-alcohols such as benzaldehyde, formaldehyde solution, methyl ethyl ketone, diacetone alcohol, acetone, cyclohexanone, mesityl oxide, and methyl isobutyl ketone; lactams or lactones such as N-methyl-2-pyrrolidone, N-vinyl-2-pyrrolidone, 2-pyrrolidone, and butyrolactone; hydrocarbons such as benzene, toluene, xylene, hexane, mineral spirits, mineral oil, and gasoline; chlorinated hydrocarbons such as carbon tetrachloride, chlorobenzene, chloroform, ethylene dichloride, methylene chloride; nitroparaffins such as nitroethane, and nitromethane; mercaptans such as thiophenol and 2-mercapto-1-ethanol; and others such as acetic acid, pyridine and dimethyl formamide.

Preferred solvents for the AVE/MA polymers are water, methanol, propanol, isopropanol, tetrahydrofuran, methyl acetate, benzaldehyde, formaldehyde solution, methyl ethyl ketone, diacetone alcohol, N-methyl-2-pyrrolidone, N-vinyl-2-pyrrolidone, dimethyl fornamide and mixtures thereof. Compounds commonly used as plasticizers can also be used as solvents for the AVE/MA polymers. Such plasticizers include dimethyl phthalate, diethyl phthalate, dioctyl phthalate, glycercin, diethylene glycol, triethylene glycol., Igepal® CO-630, Gafac® RE-610, Sorbitol, tricresyl phosphate, dimethyl sebacate, ethyl glycolate, ethylphthalyl ethyl glycolate, and p-toluene ethyl sulfonamide.

Solvents for other adhesives such as CMC, which may be optionally included in the adhesive compositions include mixtures of water and water-miscible solvents such as ethanol and acetone. Solutions of low concentration can be made with up to 40% acetone and/or 50% alcohol. Other solvents which made be used include ethanolamines; ethylene glycol; glycerol; 1,2,6-hexanetriol; mono-, di-, and triacetin; 1,5-pentanediol; polyethylene glycol (molecular weight 600 or less); propylene glycol; and trimethylolpropane.

When the adhesive compositions are prepared by dissolving the adhesive component(s) in water and/or other solvents, various embodiments of the process includes: dissolving AVE/MA adhesives in one or more of the solvents for AVE/MA polymers; dissolving an optional adhesive in a suitable solvent and coating the resulting mixture onto the non-adhesive self-supporting layer and then optionally sifting one or more adhesives onto the coated layer. Coating the layer can be achieved by techniques commonly known in the art including extrusion, doctor blading, spraying, dipping, etc.

After the adhesive component(s) has been deposited on the layer by one of the means described above, the layer is then dried. Next, the denture adhesive composition is mechanically softened by running it through a ring-roller or micro-cracker cracker or any other suitable means. The composition is then pressed smooth in a hydraulic press or flat-roller or other suitable means. The composition is then die-cut cut into denture shapes. These shapes may facilitate application of the composition to the dentures.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES I–V

| Example # | Adhesive Component | Non-Adhesive Self-Supporting Layer |
|---|---|---|
| I | 47.5 Ca/17.5 Zn AVE/MA[a] + CMC[b] | Non-woven polyester |
| II | 47.5 Ca/17.5 Zn AVE/MA[a] + CMC[b] | Polypropylene |
| III | 47.5 Ca/17.5 Zn AVE/MA[a] + CMC[b] | Non-woven rayon |
| IV | 47.5 Ca/17.5 Zn AVE/MA[a] + CMC[b] | Cloth |
| V | 47.5 Ca/17.5 Zn AVE/MA[a] + CMC[b] | Paper |

[a]Lower alkyl vinyl ether-maleic acid neutralized with 47.5% calcium and 17.5% zinc.
[b]Carboxy methyl cellulose.

Examples I–V are prepared as follows. Wet 58" by 20" of the non-adhesive self-supporting layer with water. Uniformly coat 150 grams of the adhesive component (90 g Ca/Zn AVE/MA and 60 g CMC) onto the layer and rewet the layer with water. Dry the layer. Mechanically soften the denture adhesive composition by ring-roller, and then smooth the composition on a hydraulic press. Cut the composition into denture-shaped wafers. Moisten the wafers and apply to the dentures. This wafer is peelable from the denture and forms a sticky seal that holds the dentures in place, does not ooze, and aids in preventing food from sticking between the dentures and gums.

EXAMPLES VI–X

| Example # | Adhesive Component | | Non-Adhesive Self-Supporting Layer |
|---|---|---|---|
| | Grams Ca/Zn AVE/MA[a] + | Grams CMC[b] | |
| VI | 150 | 0 | Non-woven polyester |
| VII | 75 | 75 | Non-woven polyester |
| VIII | 60 | 90 | Cloth |

-continued

| Example # | Adhesive Component Grams Ca/Zn AVE/MA[a] + | Grams CMC[b] | Non-Adhesive Self-Supporting Layer |
|---|---|---|---|
| IX polypropylene | 37.5 | 37.5 | Non-woven |
| X | 150 | 150 | Paper |

[a]Lower alkyl vinyl ether-maleic acid neutralized with 47.5% calcium and 17.5% zinc.
[b]Carboxy methyl cellulose.

Examples VI–X are prepared as follows. Wet 58" by 20" of the non-adhesive self-supporting layer with water. Uniformly coat the amount of adhesive component (as specified above) onto the layer and rewet the layer with water. Dry the layer. Mechanically soften the denture adhesive composition by ring-roller, and then smooth the composition on a hydraulic press. Cut the compositions into denture-shaped wafers. Moisten the wafers and apply to the dentures. This wafer is peelable from the denture and forms a sticky seal that holds the dentures in place, does not ooze, and aids in preventing food from sticking between the dentures and gums.

What is claimed is:

1. A denture adhesive wafer composition comprising:
   a) a lower alkyl vinyl ether-maleic acid, anhydride or salt polymer, or mixtures thereof; and
   b) a, single, non-adhesive self-supporting layer which maintains strength and provides integrity to the composition in the presence of water or saliva.

2. The denture adhesive wafer composition of claim 1 wherein the non-adhesive self-supporting layer is selected from the group consisting of polyester, polypropylene, nylon, rayon, cellulose acetate, cloth, fibrous fleece, paper, plastic, leather, microcrystalline wax, synthetic fibers, natural fibers, and mixtures thereof.

3. The denture adhesive wafer composition of claim 1 wherein the non-adhesive self-supporting layer is in a physical form selected from the group consisting of non-woven, continuous, chopped, and combinations thereof.

4. The denture adhesive wafer composition of claim 1 wherein the non-adhesive self-supporting layer is formed by a process selected from the group consisting of un-bonded, spraybonded, spun-bonded, needle-punched, carded, thermal bonded hydroentangled, meltblown, aperture print bonded, needled, wet-laid, dry-laid, and combinations thereof.

5. The denture adhesive wafer composition of claim 1 comprising a lower alkyl vinyl ether-maleic salt polymer wherein the lower alykl vinyl ether-maleic salt polymer comprises a cationic salt function selected from the group consisting of calcium, sodium, magnesium, potassium, ammonium, zinc, strontium, iron, and mixtures thereof.

6. The denture adhesive wafer composition of claim 5 wherein the lower alkyl vinyl ether-maleic salt polymer is unmixed.

7. The denture adhesive wafer composition of claim 5 wherein the lower alkyl vinyl ether-maleic salt polymer is mixed.

8. The denture adhesive wafer composition of claim 7 wherein the cationic salt function is selected from the group consisting of calcium, zinc, and mixtures thereof.

9. The denture adhesive wafer composition of claim 1 wherein the wafer composition further comprises an adhesive material selected from the group consisting of natural gums, synthetic polymers, mucoadhesive polymers, hydrophilic polymers, natural polymers, saccharide derivatives, cellulose derivatives, and mixtures thereof.

10. The denture adhesive wafer composition of claim 9 wherein the adhesive material is selected from the group consisting of natural gums, saccharide derivatives, cellulose derivatives, karaya gum, guar gum, gelatin, algin, sodium alginate, tragacanth, chitosan, acrylamide polymers, carbopol, polyvinyl alcohol, polyamines, polyquarternary compounds, polybutenes, silicones, rubbers, petrolatum, polyvinylpyrrolidone, cationic polyacrylamide polymers, methylcellulose, sodium carboxymethylcellulose, hydroxyethylcellulose, hydroxypropylcellulose, hydroxypropylmethylcellulose, carboxymethylcellulose, and mixtures thereof.

11. The denture adhesive wafer composition of claim 10 wherein the adhesive material is carboxymethylcellulose.

12. The denture adhesive wafer composition of claim 1 further comprising a toxicologically-acceptable plasticizer.

13. The denture adhesive wafer composition of claim 12 wherein the plasticizer is selected from the group consisting of dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene toluene ethyl sulfonamide, and mixtures thereof.

14. The denture adhesive wafer composition of claim 1 further comprising one or more flavors, fragrances, sensates, and mixtures thereof.

15. The denture adhesive wafer composition of claim 14 wherein the flavors, fragrances, and sensates are selected from the group consisting of natural or artificial sweetening agents, menthol, menthyl lactate, wintergreen oil, peppermint oil, spearmint oil, leaf alcohol, 3-1-menthoxypropane-1,2-diol, paramenthane caboxyamides, and mixtures thereof.

16. The denture adhesive wafer composition of claim 1 used as a denture adhesive or bioadhesive further comprising one or more therapeutic actives suitable for mucosal or topical administration.

17. The denture adhesive wafer composition or bioadhesive of claim 16 wherein the therapeutic actives are selected from the group consisting of anesthetic, analgesic, antibiotic, anti-inflammatory, antibacterial, antimicrobial, antifungal, aromatic, antihistamine, benzaldehyde, insulin, steroid, dentinal desensitizing, anti-neoplastic, agents, and mixtures thereof.

18. The denture adhesive wafer composition of claim 1 further comprising a coating which is sticky to dry dentures wherein the coating is placed on one side of the denture adhesive composition.

19. The denture adhesive wafer composition of claim 18 wherein the coating is selected from the group consisting of polybutenes, silicones, rubbers, petrolatum, natural polymers, synthetic polymers, and mixtures thereof.

20. A denture adhesive wafer composition comprising:
   a) a lower alykl vinyl ether-maleic acid, anhydride or salt polymer, or mixtures thereof;
   b) at least one non-adhesive self-supporting layer selected from the group consisting of polyester, polypropylene, nylon, rayon, cellulose acetate, cloth, fibrous fleece, paper, plastic, leather, microcrystalline wax, synthetic fibers, natural fibers, and mixtures thereof; wherein the self-supporting layer provides integrity for the composition in the presence of water or saliva; and
   c) optionally one or more additional adhesives consisting essentially of natural gums, saccharide derivatives, cellulose derivatives, karaya gum, guar gum, gelatin, algin, sodium alginate, tragacanth, chitosan, acrylamide polymers, carbopol, polyvinyl alcohol, polyamines, polyquarternary compounds, polybutenes, silicones, rubber, petrolatum, polyvinylpyrrolidone, cationic polyacrylamide polymers, methylcellulose, sodium carboxymethylcellulose, hydroxyethylcellulose, hydroxypropylcellulose, hydrox-propylmethylcellulose, carboxymethylcellulose, and mixtures thereof.

21. The denture adhesive wafer composition of claim 20 wherein the additional adhesive is selected from the group consisting of natural gums, saccharide derivatives, cellulose derivatives, polyvinyl alcohol, and mixtures thereof.

22. The denture adhesive wafer composition of claim 21 wherein the additional adhesive is selected from the group consisting of hydroxyethylcellulose, hydroxypropylcellulose, hydroxypropylmethylcellulose, carboxymethylcellulose, and mixtures thereof.

23. The denture adhesive wafer composition of claim 22 wherein the additional adhesive is carboxymethylcellulose.

24. The denture adhesive wafer composition of claim 20 comprising a lower alkyl vinyl ether-maleic salt polymer which is mixed and comprises a cationic salt function selected from the group consisting of calcium, sodium, magnesium, potassium, ammonium, zinc, strontium, iron, and mixtures thereof.

25. The denture adhesive wafer composition of claim 24 wherein the cationic salt function is selected from the group consisting of calcium, zinc, and mixtures thereof.

26. The denture adhesive wafer composition of claim 20 wherein the non-adhesive self-supporting layer is in a physical form selected from the group consisting of non-woven, woven, continuous, chopped, and combinations thereof.

27. The denture adhesive wafer composition of claim 20 wherein the non-adhesive self-supporting layer is formed by a process selected from the group consisting of un-bonded, spraybonded, spun-bonded, needle-punched, carded, thermal bonded hydroentangled, meltblown, aperture print bonded, needled, wet-laid, dry-laid, and combinations thereof.

28. The denture adhesive wafer composition of claim 20 further comprising a toxicologically-acceptable plasticizer.

29. The denture adhesive wafer composition of claim 28 wherein the plasticizer is selected from the group consisting of dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof.

30. The denture adhesive wafer composition of claim 20 further comprising one or more flavors, fragrances, sensates, and mixtures thereof.

31. The denture adhesive wafer composition of claim 30 wherein the flavors, fragrances, and sensates are selected from the group consisting of natural or artificial sweetening agents, menthol, menthyl lactate, wintergreen oil, peppermint oil, spearmint oil, leaf alcohol, 3-1-menthoxypropane-1,2-diol, paramenthane caboxyamides, and mixtures thereof.

32. The denture adhesive wafer composition of claim 20 used as a denture adhesive or bioadhesive further comprising one or more therapeutic actives suitable for mucosal or topical administration.

33. The denture adhesive wafer or bioadhesive of claim 32 wherein the therapeutic actives are selected from the group consisting of anesthetic, analgesic, antibiotic, anti-inflammatory, antibacterial, antimicrobial, antifungal, aromatic, antihistamine, benzaldehyde, insulin, steroid, dentinal desensitizing, anti-neoplastic, agents, and mixtures thereof.

34. The denture adhesive wafer composition of claim 20 further comprising a coating which is sticky to dry dentures wherein the coating is placed on one side of the denture adhesive composition.

35. A process for the preparation of the denture adhesive wafer composition of claim 1 wherein the denture adhesive wafer composition is mechanically softened and pressed smooth and cut into denture shapes.

36. A process for the preparation of the denture adhesive wafer composition of claim 20 wherein the denture adhesive wafer composition is mechanically softened and pressed smooth and cut into denture shapes.

37. A process for preparing a denture adhesive wafer comprising the steps of:
 a) mixing at least one adhesive component with one or more solvents to create a mixture; and
 b) applying the mixture onto a non-adhesive self-supporting layer.

38. The process of claim 37 wherein the solvent is selected from the group consisting of water, methanol, propanol, isopropanol, tetrahydrofuran, methyl acetate, benzaldehyde, formaldehyde solution, methyl ethyl ketone, diacetone alcohol, N-methyl-2-pyrrolidone, N-vinyl-2-pyrrolidone, dimethyl formamide, and mixtures thereof.

39. The process of claim 37 which further comprises the step of sifting one or more adhesive components onto the layer.

40. The process of claim 39 further comprising re-applying the mixture onto the layer.

41. The process of claim 40 further comprising re-applying the mixture onto the layer multiple times.

42. The process of claim 41 which further comprises the steps of drying the layer after the mixture has been applied, mechanically softening and pressing smooth the layer, and cutting the layer into denture shapes.

* * * * *